United States Patent
Bentley et al.

(10) Patent No.: US 6,541,015 B2
(45) Date of Patent: Apr. 1, 2003

(54) HYDROLYTICALLY DEGRADABLE CARBAMATE DERIVATIVES OF POLY(ETHYLENE GLYCOL)

(75) Inventors: Michael David Bentley, Huntsville, AL (US); Xuan Zhao, Huntsville, AL (US)

(73) Assignee: Shearwater Corporation, Huntsville, AL (US)

( * ) Notice: Subject to any disclaimer, the term of this patent is extended or adjusted under 35 U.S.C. 154(b) by 0 days.

(21) Appl. No.: 09/842,514

(22) Filed: Apr. 26, 2001

(65) Prior Publication Data

US 2001/0046481 A1 Nov. 29, 2001

Related U.S. Application Data

(62) Division of application No. 09/469,418, filed on Dec. 23, 1999, now Pat. No. 6,413,507.

(51) Int. Cl.$^7$ .......................... A61K 9/00; A61K 37/74; C08B 37/02
(52) U.S. Cl. ................ 424/400; 429/78.02; 429/78.08; 429/78.18; 429/78.31; 435/820; 530/350; 536/112; 536/123.1
(58) Field of Search .............................. 424/78.02, 400, 424/78.08, 78.18, 78.31; 536/112, 123.1; 530/350; 435/820

(56) References Cited

U.S. PATENT DOCUMENTS

| | | |
|---|---|---|
| 4,760,057 A | 7/1988 | Alexander |
| 4,935,465 A | 6/1990 | Garman |
| 5,413,992 A | 5/1995 | Nicolaou et al. |
| 5,561,119 A | 10/1996 | Jacquesy et al. |
| 6,011,042 A | 1/2000 | Greenwald et al. |

FOREIGN PATENT DOCUMENTS

| | | |
|---|---|---|
| EP | 0 595 133 A2 | 10/1993 |
| WO | WO 90/13540 | 11/1990 |
| WO | WO 96/23794 A1 | 8/1996 |
| WO | WO 99/30727 A | 6/1999 |

OTHER PUBLICATIONS

Greenwald et al., "Poly(ethylene glycol) conjugated drugs and prodrugs: a comprehensive review,"*Critical Review in Therapeutic Drug Carrier Systems*, 2000, 17(2) 101–61, Ref. 147.
Greenwald et al., "Drug delivery systems based on trimethyl lock lactonization: poly(ethylene glycol) prodrugs of amino–containing compounds," *Journal of Medicinal Chemistry*, Feb. 10, 2000, 43 (3) 475–87.
Greenwald, R.B., "Drug delivery systems: anticancer prodrugs and their polymeric conjugates", *Exp. Opin. Ther. Patents*, 7(6):601–609 (1997).
Bentley et al., "PEG–linked Artemisinin Antimalarials", *Polymer Preprints*, 38(1):584–585 (1997).
Zalipsky, "Chemistry of polyethylene glycol conjugates with biologically active molecules", *Advanced Drug Delivery Reviews*, 16:157–182 (1995).
Zalipsky et al., "Attachment of Drugs to Polyethylene Glycols,"*European Polymer Journal*, 19(12): 1177–1183 (1983).
Larwood and Szoka, "Synthesis, Characterization, and in vivo Disposition of Iodinatable Polyethylene Glycol Derivatives: Differences in vivo as a Function of Chain Length",*J. Labeled Compd. Radiopharm.*, 21:603–614 (1984).
Ouchi et al., "Design of Antitumor Agent–Terminated Poly-(Ethylene Glycol) Conjugate as Macromolecular Prodrug,"*Polymer Preprints*, 38(1):582–583 (1997).
Greenwald et al., "Drug Delivery Systems Employing 1,4– or 1,6–Elimination: Poly(ethylene glycol) Prodrugs of Amine–Containing Compounds", *J. Med. Chem.*, 42:3657–3667 (1999).

*Primary Examiner*—Elli Peselev
(74) *Attorney, Agent, or Firm*—Alston & Bird LLP (57) ABSTRACT

Poly(ethylene glycol) carbamate derivatives useful as water-soluble pro-drugs are disclosed. These degradable poly (ethylene glycol) carbamate derivatives also have potential applications in controlled hydrolytic degradation of hydrogels. In such degradable hydrogels, drugs may be either trapped in the gel and released by diffusion as the gel degrades, or they may be covalently bound through hydrolyzable carbamate linkages. Hydrolysis of these carbamate linkages releases the amine drug at a controllable rate as the gel degrades.

38 Claims, 1 Drawing Sheet

Figure 1.

HYDROLYTICALLY DEGRADABLE CARBAMATE DERIVATIVES OF POLY(ETHYLENE GLYCOL)

CROSS-REFERENCE TO RELATED APPLICATIONS

This application is a divisional application of Ser. No. 09/469,418, filed Dec. 23, 1999, now U.S. Pat. No. 6,413,507 B1.

FIELD OF THE INVENTION

This invention relates to hydrolyzable derivatives of poly (ethylene glycol) useful as prodrugs and as degradable components of cross-linked polymers.

BACKGROUND OF THE INVENTION

Covalent attachment of the hydrophilic polymer, poly (ethylene glycol), commonly referred as PEG, to biologically active agents and surfaces has important applications in biotechnology and medicine.

PEG is generally soluble in water and many organic solvents. PEG is also substantially non-toxic and normally does not elicit any significant immune response in animals. When PEG is chemically attached to a water insoluble compound, the resulting conjugate generally is soluble in water as well as in many organic solvents. When the agent to which PEG is attached is biologically active, such as a drug, the activity of the agent can be retained after the attachment of PEG, and the conjugate generally displays altered pharmacokenetics.

The prodrug approach, in which drugs are released by degradation of more complex agents (prodrugs) under physiological conditions, is a powerful component of drug delivery. See R. B. Greenwald, *Exp. Opin. Ther. Patents,* 7(6) :601–609 (1997). Prodrugs can, for example, be formed by bonding PEG to drugs using linkages which are degradable under physiological conditions.

However, not all linkages are readily degradable and useful in prodrug applications. In general, ester linkages, formed by condensation reactions between PEG carboxylic acids or activated PEG carboxylic acids and alcohol groups on drugs, hydrolyze under physiological conditions to release the drug. For example, in PCT Publication No. WO 96/23794, it is disclosed that paclitaxel can be linked to PEG using ester linkages and the linked paclitaxel can be released in serum by hydrolysis. Antimalarial activity of dihydroartemisinin bonded to PEG through a hydrolyzable ester linkage has also been demonstrated. Bentley et al., *Polymer Preprints,* 38(1):584(1997).

Conventional amide and carbamate linkages, formed with amine groups on drugs, generally are stable and do not hydrolyze to release a free drug within a sufficiently short time that is required in practical applications. See, e.g., Zalipsky, *Advanced Drug Delivery Reviews,* 16:157–182 (1995); Zalipsky, et al., *Eur. Polym. J.,* 19:1177–1183 (1983). For example, it has been demonstrated that carbamate linkages between PEG and a protein in a conjugate are stable under a variety of physiological conditions. Larwood and Szoka, *J. Labeled Compd. Radiopharm.* 21:603 (1984). Many useful drugs including peptides, proteins, and small agents having amine groups have been bonded to PEG through non-hydrolyzable amide and carbamate linkages. PEG can also be bonded to amine groups on drugs through reductive amination with PEG aldehydes and the resulting amine linkage is non-degradable in vivo.

Because many drugs such as proteins have amine groups that are readily available for reaction to form linkages, it is desirable to make such linkages hydrolytically degradable so that free proteins or other amine-containing agents can be released from the prodrugs at a controlled rate in vivo. Imines, or Schiff bases, offer a possible approach since they hydrolyze to generate the free amine and an aldehyde:

where R' is a drug or other agent bearing an amino group. This approach has been used in attaching doxorubicin to PEG with release of the drug occurring by hydrolysis of the imine linkage. Ouchi et al. *Polymer Preprints,* 38(1):582–3 (1997). Since the formation of imines is reversible in water, these compounds are best prepared in organic solvents. Many proteins, peptides, and other agents are thus not amenable to the imine prodrug approach because of their poor solubility or instability in organic solvents.

Conjugates can be prepared by linking an amine-containing drugs through a non-hydrolyzable amide or carbamate linkage, to a PEG molecule having hydrolytically degradable linkages in the PEG backbone. The amine-containing drug is releasable upon the degradation of the PEG backbone. However, the released drug usually has a fragment attached through an amide or carbamate linkage, and the native or parent drug is not released.

U.S. Pat. No. 4,935,465 discloses a water-soluble prodrug in which neighboring group participation by a carboxyl group aids in the hydrolysis of an amide, thus releasing the drug. PEG was a component of a bovine serum albumin (BSA) prodrug disclosed in that patent:

U.S. Pat. No. 5,561,119 and European Patent No. 595133-A disclose a doxorubicin prodrug as shown below, which utilizes a benzylglucuronyl carbamate linkage. A second component, glucuronidase, must be added in order to cleave the glucuronic acid and liberate doxorubicin and a nitrobenzoquinone methide.

In yet another approach as disclosed in U.S. Pat. No. 5,413,992, a prodrug of daunamycin shown below, liberates the native drug by an enzyme-induced elimination initiated by abstraction of a proton adjacent to the sulfone group.

In addition, U.S. Pat. No. 4,760,057 describes enzymatic hydrolysis of a prodrug containing a carbamate linkage:

where RR'N represents the secondary amine on a drug moiety, and $R_{1-3}$ are various moieties such as hydrogen, alkyls, or cycloalkyls. Such prodrugs are hydrolyzed by esterases to generate $RR'NCO_2CR_1R_2OH$ which then decomposes to liberate the drug agent.

Greenwald et al. *J. Med. Chem.*, 42:3657–3667 (1997) discloses prodrugs having a drug linked, through a carbamate linkage to a PEG derivative. 1,4 or 1,6 elimination reaction is required to release the free drug. The prodrug is structurally complex and toxic quinone methide intermediates may be liberated along the free drug.

Thus, the prodrugs in the prior art generally have drawbacks that limit their practical applications. The requirement for enzyme digestion makes the prodrugs unsuitable or at least less useful for in vivo use. In addition, the generation of toxic intermediates can be associated with the release of free drugs. Thus, there remains a need for prodrugs having improved characteristics.

SUMMARY OF THE INVENTION

The invention provides a water soluble prodrug in which a biologically active agent is linked to a water soluble non-immunogenic polymer by a hydrolyzable carbamate bond. The biologically active agent can be readily released by the hydrolysis of the carbamate bond in vivo without the need for adding enzymes or catalytic materials. Generally, the biologically active agent is released, upon hydrolysis, into its parent state, i.e., without any additional moieties attached thereto. In addition, because a water soluble, non-peptidic polymer is used, even a substantially insoluble biologically active agent can be readily delivered in the prodrug in vivo.

Thus, in accordance with the present invention, a prodrug is provided having the formula:

wherein POLY is a water soluble and non-peptidic polymer, L is a linking group, Ar is an aromatic group, and Y is a biologically active agent.

The water soluble non-immunogenic polymer can have a capping group selected from the group consisting of OH, alkoxy, and wherein L' is a linking group, Ar' is an aromatic group, and Y' is a biologically active agent. Preferably, POLY is a poly(ethylene glycol) or a derivative thereof having a molecular weight of from about 200 to about 100,000 Daltons.

In accordance with another embodiment of the invention, a compound is provided having the formula:

in which POLY is a water soluble, non-peptidic polymer, L is a linking group, Ar is an aromatic group, and X is an activating group capable of reacting with an amino group of a biologically active agent to form a carbamate linkage.

Optionally, POLY can have a capping group selected from the group consisting of OH, alkoxy, and wherein L' is a linking group, Ar' is an aromatic group, and X' is an activating group capable of reacting with an amino group of a biologically active agent to form a carbamate linkage. Preferably, POLY is a poly(ethylene glycol) or a derivative thereof having, a molecular weight of from about 200 to about 100,000 Dalton.

In another embodiment of this invention, a prodrug is provided having the formula:

where Y is a biologically active agent having an aromatic group, Ar is the aromatic group of the biologically active agent Y, such as a substituted benzene or other aromatic such as a substituted naphthalene or heterocyclic moiety, and POLY is a water soluble, non-peptidic polymer, preferably poly(ethylene glycol) in any of its forms. Hydrolysis of this derivative yields the parent drug Y—ArOH, and POLY—NH$_2$ and CO$_2$.

In accordance with yet another embodiment of the present invention, a hydrolytically degradable hydrogel is provided. The hydrogel comprises a backbone bonded to a crosslinking agent through a hydrolyzable carbamate linkage. Typically, a suitable backbone can be any compound having an amino group, preferably at least two amino groups. Examples of such backbones include, but are not limited to, proteins, peptides, aminocarbohydrates, aminolipids, poly(vinylamine), polylysine, poly(ethylene glycol) amines, pharmaceutical agents having an amino group, etc. The crosslinking agent is selected from the group consisting of:

and wherein POLY is a non-peptidic, water soluble polymer, L and L' are linking groups, Ar and Ar' are aromatic groups, Z is a central branched core, n is from 2 to about 100, and X and X' are activating groups capable of reacting with the amino groups in the backbone to form hydrolyzable carbamate linkages. Preferably, POLY is a poly(ethylene glycol) or derivative thereof having a molecular weight of from about 200 to about 100,000.

The foregoing and other features and advantages of the invention, and the manner in which the same are accomplished, will be more readily apparent upon consideration of the following detailed description of the invention in conjunction with the claims and the drawings.

DETAILED DESCRIPTION OF THE INVENTION

As used herein, the term "prodrug" means a chemical derivative of a biologically active agent which can release or liberate the parent biologically active agent under defined conditions. By converting a parent biologically active agent into a prodrug, the solubility and immunogenicity of the agent can be modified. In addition, by controlling the rate of release of the agent from the prodrug, temporal control of the agent's action in vivo can be achieved.

The term "biologically active agent" when used herein means any substances which can affect any physical or biochemical properties of a biological organism including but not limited to viruses, bacteria, fungi, plants, animals and humans. In particular, as used herein, biologically active agent includes any substance intended for the diagnosis, cure, mitigation, treatment, or prevention of disease in humans or other animals, or to otherwise enhance physical or mental well being of humans or animals. Examples of biologically active agents include, but are not limited to, organic and inorganic compounds, proteins, peptides, lipids, polysaccharides, nucleotides, DNAs, RNAs, other polymers, and derivatives thereof. Examples of biologically active agents also include, e.g., antibiotics, fingicides, anti-viral agents, anti-inflammatory agents, anti-tumor agents, cardiovascular agents, anti-anxiety agents, hormones, growth factors, steroidal agents, and the like.

A prodrug of this invention has the formula:

wherein:

POLY is a substantially non-immunogenic water soluble polymer;

L is a covalent linkage, preferably a hydrolytically stable linkage;

Ar is an aromatic group; and

Y is a biologically active agent.

As used herein, the terms "group," "functional group," "active moiety," "reactive site," reactive groups" and "reactive moiety" are all somewhat synonymous in the chemical arts and are used in the art and herein to refer to distinct, definable portions or units of a agent and to units that perform some function or activity and are reactive with other agents or portions of agents.

The term "linking group" is used to refer to groups that normally are formed as the result of a chemical reaction and typically involve covalent bonding.

In the prodrug of this invention, the substantially water soluble non-immunogenic polymer POLY is preferably poly(ethylene glycol) (PEG). However, it should be understood that other related polymers are also suitable for use in the practice of this invention and that the use of the term PEG or poly(ethylene glycol) is intended to be inclusive and not exclusive in this respect.

Poly(ethylene glycol) or PEG is useful in biological applications because it has properties that are highly desirable and is generally approved for biological or biotechnical applications. PEG typically is colorless, odorless, soluble in water, stable to heat, inert to many chemical agents, does not hydrolyze or deteriorate, and is generally nontoxic. Poly(ethylene glycol) is considered to be biocompatible, which is to say that PEG is capable of coexistence with living tissues or organisms without causing harm. More specifically, PEG normally does not tend to produce an immune response in the body. When attached to an agent having some desirable function in the body, the PEG tends to mask the agent and can reduce any immune response so that an organism can tolerate the presence of the agent. Accordingly, the prodrug of the invention typically is substantially non-toxic and does not tend to produce substantial immune response or cause clotting or other undesirable effects. PEG having the formula —CH$_2$CH$_2$—(CH$_2$CH$_2$O)$_n$—CH$_2$CH$_2$—, where n is from about 8 to about 4000, is one useful polymer in the practice of the invention. Preferably PEG having a molecular weight of from about 200 to about 100,000 Da is used as POLY.

In its most common form, PEG is a linear polymer having a hydroxyl group at each terminus:

HO—CH$_2$—CH$_2$O(CH$_2$CH$_2$O)$_n$CH$_2$CH$_2$—OH

PEG is commonly used as methoxy-PEG, or mPEG in brief, in which one terminus is the relatively inert methoxy group, while the other terminus is a hydroxyl group that is subject to ready chemical modification:

CH$_3$O—(CH$_2$CH$_2$O)$_n$—CH$_2$CH$_2$—OH

Branched PEGs are also in common use. The branched PEGs can be represented as R(—PEG—OH)$_m$ in which R represents a central core agent such as pentaerythritol or glycerol, and m represents the number of arms. The number of arms m can range from three to a hundred or more. The hydroxyl groups are subject to ready chemical modification.

Another branched form of PEG can be represented as (CH$_3$O—PEG—)$_p$R—Z, where p equals 2 or 3, R represents a central core such as lysine or glycerol, and Z represents a group such as carboxyl that is subject to ready chemical activation. This type of PEG has a single terminus that is subject to ready chemical modification.

Yet another branched form, the pendant PEG, has reactive groups, such as carboxyls, along the PEG backbone rather than at the end of PEG chains.

Forked PEG represented by the formula PEG(—LCHX$_2$)$_n$ is another form of branched PEG, where L is a linking group and X is an activated terminal group.

In addition, the polymers can also be prepared to have weak or degradable linkages in the backbone. For example, PEG having hydrolytically unstable ester linkages in the polymer backbone can be prepared. The ester linkages are susceptible to hydrolysis which results in cleavage of the polymer into fragments of lower molecular weight:

—PEG—CO$_2$—PEG—+H$_2$O→—PEG—CO$_2$H+HO—PEG—

It is understood by those skilled in the art that the term poly(ethylene glycol) or PEG represents or includes all the above forms.

Other polymers than PEG are also suitable for the present invention. These other polymers include, but are not limited to, other poly(alkylene oxides) such as poly(propylene glycol) ("PPG"), copolymers of ethylene glycol and propylene glycol and the like; poly(oxyethylated polyols) such as poly(oxyethylated glycerol), poly(oxyethylated sorbitol), and poly(oxyethylated glucose); poly(vinyl alcohol) ("PVA"); dextran; carbohydrate-based polymers and the like. The polymers can be homopolymers or random or block copolymers and terpolymers based on the monomers of the above polymers, straight chain or branched.

Specific examples of suitable additional polymers include, but are not limited to, poly(oxazoline), difunctional poly(acryloylmorpholine) ("PAcM"), and poly (vinylpyrrolidone)("PVP"). PVP and poly(oxazoline) are well known polymers in the art and their preparation should be readily apparent to the skilled artisan. PAcM and its synthesis and use are described in U.S. Pat. Nos. 5,629,384 and 5,631,322, the contents of which are incorporated herein by reference in their entirety.

Although the molecular weight of POLY can vary, it is typically in the range of from about 100 to about 100,000, preferably from about 2,000 to about 80,000.

Those of ordinary skill in the art will recognize that the foregoing list for substantially water soluble non-immunogenic polymer POLY is by no means exhaustive and is merely illustrative, and that all polymeric materials having the qualities described above are contemplated.

The polymer POLY can have a terminal capping group distal to the biologically active agent Y. Examples of the capping group include, but are not limited to, OH, alkoxy, and wherein L' is a hydrolytically stable linkage, Ar' is an aromatic group, and Y' is a biologically active agent. L', Ar', and Y' can be same or different from L, Ar, and Y respectively.

The aromatic groups Ar and Ar' in the prodrug can be any aryl groups in any chemically arranged forms. For example, phenyl, substituted phenyl, biphenyl, substituted biphenyl, polycyclic aryls, substituted polycyclic aryls, heterocyclic aryls, substituted heterocylic aryls, and derivatives thereof can all be used. The substitutions on the aromatic ring(s) of Ar and Ar' can be at any position relative to L or L'. Examples of suitable substitution moieties include, but are not limited to, halogen, alkyls, alkoxy, hydroxy, carboalkoxy and carboxamide. It should be understood that these additional groups bonded to the aromatic group may affect the hydrolysis rate of the carbamate linkage between Ar and Y, and/or Ar' and Y'. Thus, different substitution moieties can be chosen to control the release rate of the biologically active agent Y and Y'. Preferably Ar and Ar' are benzenes or substituted benzenes.

The linking groups L and L' link the aromatic groups Ar and Ar', respectively, to the non-immunogenic polymer POLY. Typically they are formed by reacting a terminal group of POLY with a reactive moiety on a ring of the aromatic group Ar or Ar'. L and L' can be any covalent linkages. In particular, L and L' can include covalent bonds such as ethers, amines, imines, imides, amides, carbamides, esters, thioesters, carbonates and ureas. For example, L and L' can be selected from moieties such as —O—, —NR— where R is H, a C$_{1-6}$ alkyl or substituted alkyl, —CO$_2$—, —O$_2$C—, —O$_2$CO—, —CONH—, —NHCO—, —S—, —SO—, —SO$_2$—, etc. Preferably L and L' are —O—, or —NHCO—.

The carbamate linkages between Ar and Y, and Ar' and Y' are hydrolyzable in vivo at a desirable rate. Typically, when a prodrug of this invention is delivered into the body, the prodrug is first delivered to the desired tissue or organ through a selected route, e.g., blood circulation. The parent biologically active agent is released by hydrolysis. Once the parent agent is released, the rest of the components of the prodrug are subsequently eliminated by biodegradation or excretion. To achieve the optimal result the linkages L and L' typically are more stable than the hydrolyzable carbamate linkage. Preferably, L and L' are hydrolytically stable linkages. In addition, the prodrug circulation lifetime should be longer than the time required for hydrolysis of the carbamate linkage.

In the prodrug of this invention, the release rate of the parent biologically active agent from the prodrug can be modified in a number ways. It has been found that the rate of hydrolytic degradation of the carbamate linkage is affected by the position of the attachment of the L or L', as defined above, to the aromatic ring relative to the position of the carbamate linkage attachment. That is, the carbamate hydrolysis rates vary, in the case of benzene derivatives, between ortho, meta, and para placement of L or L'. The rate of hydrolysis of the carbamate linkage is also affected by the nature of L and L', for example an ether linkage is more stable than an amide linkage. Moreover, additional moieties bonded to the aromatic group may affect the hydrolysis rate of the carbamate linkage. Thus, different substitution moieties can be chosen to control the release rate of the biologically active agent Y and Y'.

In one preferred embodiment, the prodrug of this invention has the formula:

wherein:

L is —O— or —NHCO—;

Y is a biologically active agent;

POLY is poly(ethylene glycol) having a capping group selected from the group consisting of —OH, $C_{1-4}$ alkoxy, and wherein Y' and L' are as described above.

Thus, the hydrolysis of the carbamate linkage in the prodrug can be illustrated as follows:

Although, the present invention is especially suited for delivering biologically active agents that are water insoluble and/or immunogenic, this invention can be used for virtually any biologically active agents. However, as is clear below in the description of the synthesis of the prodrug, the biologically active agent to be converted to the prodrug of this invention must have an amino group or a moiety that can be converted to an amino group. Suitable biologically active agents include, but are not limited to, proteins, enzymes, peptides, aminolipids, polysaccharides having an amino group, amino-oligonucleotides, and pharmaceutical agents having an amino group.

Generally the method of synthesizing a prodrug of this invention includes the following steps: first, an activated water soluble and non-peptidic polymer is provided. The activated polymer typically has a reactive terminal moiety. For example, the activated polymer can be POLY—$NH_2$, $H_2N$—POLY—$NH_2$, POLY—O—$SO_2$—$CH_3$, or $CH_3$—$SO_2$—O—POLY—O—$SO_2$—$CH_3$, and the like. An aryl compound having two reactive substitution groups linked to the aromatic ring is also provided. The aryl compound can be, e.g., hydroxybenzoic acid or benzyloxyphenol. One of the two reactive groups on the aromatic ring can react with the reactive terminal moiety of the activated polymer to form the linkage L. The other reactive group of the aryl compound either itself can react with an amino group of a biological active agent to form a hydrolyzable carbamate linkage, or can be converted into a reactive group which can react with an amino group of a biological active agent to form a hydrolyzable carbamate linkage. Thus, a compound is provided having the formula:

wherein POLY, L, and Ar are as described in regard to the prodrug of this invention, and wherein X is an activating group capable of reacting with an amino group of a biologically active agent to form a hydrolyzable carbamate linkage.

Preferably, L is —O— or —NHCO—, Ar is a substituted or unsubstituted benzene moiety, X is chlorine, bromine, N-succinimidyloxy, or 1-benzotriazolyloxy, and POLY is poly(ethylene glycol) or a derivative thereof with a molecular weight of from about 200 to about 100,000 Dalton and having a capping group selected from the group consisting of —OH, $C_{1-4}$ alkoxy, and where L' is —O— or —NHCO—, Ar' is a substituted or unsubstituted benzene moiety, and X' is chlorine, bromine, N-succinimidyloxy, or 1-benzotriazolyloxy.

In another embodiment of this invention, a prodrug is provided having the formula:

Y—Ar—O—C(O)—NH—POLY where Y is a biologically active agent having an aromatic group, Ar is the aromatic group of the biologically active agent Y, such as a substituted benzene or other aromatic such as a substituted naphthalene or heterocyclic moiety, and POLY is a water soluble, non-peptidic polymer as described above, preferably poly(ethylene glycol) in any of its forms. Hydrolysis of this derivative yields the parent drug Y—ArOH, and POLY—$NH_2$ and $CO_2$.

In accordance with another aspect of this invention, a hydrolytically degradable hydrogel is provided. The hydrogel comprises a backbone bonded to a crosslinking agent through a hydrolyzable carbamate linkage.

Typically, the backbone of the hydrogel is a biocompatible macromolecule. The backbone has an amino group available to react with the crosslinking agent to form a hydrolyzable carbamate linkage. Preferably, the backbone has at least two of such amino groups. Examples of such backbones include, but are not limited to, proteins, modified proteins such as glycoproteins, phosphorylated proteins, acylated proteins, and chemically modified proteins, peptides, aminocarbohydrates, glycosaminoglycans, aminolipids, poly(vinylamine), polylysine, poly(ethylene glycol) amines, pharmaceutical agents having at least two amino groups, etc. Specific examples of the backbone include, but are not limited to, fibrin, fibrinogen, thrombin, albumins, globulins, collagen, fibronectin, chitosan and the like. In addition, the backbone may also be microorganisms such as viral particles, bacterial cells, or animal or human cells.

The crosslinking agent can be the difunctional polymer described above having the formula:

wherein POLY, L, L', X, X', Ar, and Ar' are as described above. Alternatively, the crosslinking agent can also be a branched water-soluble substantially non-immunogenic polymer having the formula:

wherein POLY, L, Ar, and X are as described above, Z is a central branched core moiety, and n represents the number of arms and is from 2 to about 100. In particular, the central branched core moiety can be derived from the amino acid lysine, or polyols such as glycerol, pentaerythritol and sorbitol. Branched PEGs are known in the art. Suitable branched PEGs can be prepared in accordance with U.S. Pat. No. 5,932,462, which is incorporated herein in its entirety by reference. These branched PEGs can then be modified in accordance with the present teachings. For example, a four-arm, branched PEG prepared from pentaerythritol is shown below:

$$C(CH_2-OH)_4 + n\ C_2H_4O \rightarrow C[CH_2O-(CH_2CH_2O)_n-CH_2CH_2-OH]_4$$

This branched PEG can then be further modified to form the branched crosslinking agent by the method as described above in the context of synthesizing a prodrug.

In a preferred embodiment, the crosslinking agent has the formula:

wherein X and L are as described above. Thus, the crosslinking of a backbone having multiple amino groups by this crosslinking agent in the process for forming a hydrogel can be illustrated as follows:

where the zig-zag notation represents a backbone having amine groups and where L is as described above.

As will be apparent, the carbamate linkages between the backbones and the crosslinking agents formed from the crosslinking reactions are hydrolyzable. Thus, the hydrogel of this invention can gradually break down or degrade in the body as a result of the hydrolysis of the carbamate linkages. Therefore, the hydrogel of this invention can be used as a carrier for delivery of biologically active agents and other suitable biomedical applications. For example, the hydrogel can carry therapeutic drugs and can be implanted or injected in the target area of the body. The hydrogel may also carry other agents such as nutrients or labeling agents for imaging analysis.

In the various applications of the hydrogel of this invention, the biologically active agents to be delivered can be used as the backbone, or part of the backbone of the hydrogel. Alternatively, biologically active agents can be in the form of a prodrug as described above and covalently linked to the hydrogel as illustrated:

wherein L is a linkage as described above, Y is a biologically active agent to be delivered in the hydrogel. Typically, in this case, Y has an amino group which can react and form a carbamate linkage as described above. Also, biologically active agents or other substances to be delivered can also be loaded into the hydrogel during the synthesis of the hydrogel, or afterwards, e.g., by diffusion into the cavity or matrix of the hydrogel without being covalently bonded to the hydrogel structure, that is, the backbone or crosslinking agent of the hydrogel.

Because the crosslinking agents in the hydrogel are water soluble and substantially non-immunogenic, the hydrogel can be substantially water soluble and non-immunogenic as well. In addition, because of the interconnection by a large number of hydrolytically degradable carbamate linkages, typically the degradation or breakdown of the hydrogel in the body is gradual in nature. Thus, it is particularly useful for sustained release of a biologically active agent or other substances in the body.

The present invention is further illustrated in the following examples which are given to illustrate the invention, but should not be considered in limitation of the invention.

EXAMPLES

Example 1

Synthesis of N-mPEG benzamide-m-succinimidyl Carbonate (1)

-continued mPEG amine 5000 (1.5 g, 0. 3 mmole), 3-hydroxybenzoic acid (44 mg, 0.315 mmole) and dicyclohexylcarbodiimide (DCC, 84 mg) were dissolved in 20 ml of anhydrous THF. The solution was stirred at room temperature overnight. The solvent was condensed to half on a rotary evaporator and the residue was precipitated into 150 ml of ethyl ether. The precipitate was collected by filtration and dried in vacuo. Yield 1.5 g (100%). $^1$H NMR(DMSO—$d_6$): $\delta$ 3.5 (br m, PEG), 6.90 (m, aromatic), 7.22 (m, aromatic), 8.3–7 (t, PEG—N$\underline{H}$CO—), 9.62 (s, —$C_6H_6$—O$\underline{H}$).

The above product (1 gram) and disuccinimidyl carbonate (DSC, 200 mg) were dissolved in 8 ml of acetonitrile. To the solution was added 200 ul of pyridine. The solution was stirred under nitrogen overnight and the solvent was removed under reduced pressure. The resulting solid was redissolved in 10 ml of dry chloroform and the insoluble solid was removed by filtration. The solution was then precipitated into 150 ml of dry ethyl ether and the precipitate collected by filtration and dried in vacuo. Yield 0.95 g (95%). $^1$H NMR(DMSO—$d_6$): $\delta$ 3.5 (br m, PEG), 7.58 (m, aromatic), 7.83 (m, aromatic), 8.64 (t, PEG—N$\underline{H}$CO—).

Example 2
Synthesis of N-mPEG-benzamide-p-succinimidyl Carbonate (2)

mPEG amine 5000 (3 g, 0.6 mmole), 4-hydroxybenzoic acid (87 mg, 0.62 mmole) and dicyclohexylcarbodiimide (DCC, 160 mg) were dissolved in 20 ml anhydrous THF. The solution was stirred at room temperature overnight. The solvent was condensed to half on a rotary evaporator and the residue was precipitated into 150 ml of ethyl ether. The precipitate was collected by filtration and dried in vacuo. Yield 3 g (100%). $^1$H NMR(DMSO—$d_6$): $\delta$ 3.5 (br m, PEG), 6.78 (d, aromatic), 7.70 (d, aromatic), 8.23 (t, PEG—N$\underline{H}$CO—), 9.94 (s, —$C_6H_6$—O$\underline{H}$).

The above product (1.5 gram) and disuccinimidyl carbonate (DSC, 300 mg) were dissolved in 12 ml of acetonitrile. To the solution was added 300 ul of pyridine. The solution was stirred under nitrogen overnight and the solvent was removed under reduced pressure. The resulting solid was redissolved in 10 ml of dry chloroform and the insoluble solid was removed by filtration. The solution was then precipitated into 150 ml of dry ethyl ether. The precipitate was collected by filtration and dried in vacuo. Yield 1.42 g (95%). $^1$H NMR(DMSO—$d_6$): $\delta$ 3.5 (br m, PEG), 7.49 (d, aromatic), 7.95 (d, aromatic), 8.60 (t, PEG—N$\underline{H}$CO—).

Example 3
Synthesis of mPEG Phenyl ether-1-succinimidyl Carbonate (3)

mPEG mesylate 5000 (5 g, 1 mmole) in 60 ml of toluene was azeotropically distilled under nitrogen. After two hours, the solution was cooled to room temperature. 4-benzyloxyphenol (0.44 g, 2.2 mmole) was added to a mixture of 0.46 ml of sodium methoxide (2 mmole, 25% in methanol) and 25 ml of dry methanol. The mixture was slowly stirred under nitrogen for 20 minutes. Methanol was then gradually distilled off until about 5 ml of solution was left. 50 ml of dry toluene was added and the solution was distilled under nitrogen. The azeotropic distillation was not stopped until all methanol was removed. The mixture was cooled to room temperature. The freshly azeotropically dried mPEG mesylate from the previous step was added and the mixture was refluxed under nitrogen overnight. The reaction mixture was cooled to room temperature, toluene was distilled off, and methylene chloride was added. The solid was removed by filtration and the filtrate was washed with 10% sodium bicarbonate containing 10% sodium chloride aqueous solution and then dried over sodium sulfate. The dry methylene chloride solution was filtered, condensed on a rotary evaporator and precipitated into 100 ml of ether.

The product was collected by filtration and dried in vacuum. Yield 4.5 g (90%). $^1$H NMR(DMSO—$d_6$): δ 3.5 (br m, PEG), 4.00 (t, —PEGOCH$_2$C$\underline{H}_2$OC$_6$H$_4$O—), 5.02 (s, —PEGOC$_6$H$_4$OC$\underline{H}_2$C$_6$H$_5$), 6.90 (d+d, —PEGOC$_6$$\underline{H}_4$O—), 7.35 (m, —PEGOC$_6$H$_4$OCH$_2$C$_6$$\underline{H}_5$).

mPEG -p-(benzyloxy)-phenyl ether (4.5 g, 0.9 mmole) was dissolved in 1,4-dioxane (40 ml), and then hydrogenated with H$_2$ (2 atm pressure) and 1.5 gram Pd/C (10%) overnight. The catalyst was removed by filtration and the product precipitated into ethyl ether after most solvent was distilled off on a rotary evaporator. Yield: 3.7 gram (82%). $^1$H NMR(DMSO—$d_6$): δ 3.5 (br m, PEG), 3.96 (t, —PEGOCH$_2$C$\underline{H}_2$OC$_6$H$_4$OH), 6.70 (d+d, —PEGOC$_6$$\underline{H}_4$O—), 8.89 (s, —OH).

mPEG phenyl ether-p-phenyl alcohol (1.2 g) and disuccimidyl carbonate (DSC, 210 mg) were dissolved into 15 ml of acetonitrile. To the solution was added 0.12 ml of pyridine. The solution was stirred under nitrogen overnight and the solvent was removed under reduced pressure. The resulting solid was redissolved in 10 ml of dry chloroform and the insoluble solid was removed by filtration. The solution was then precipitated into 150 ml of dry ethyl ether. The precipitate was collected by filtration and dried in vacuo. Yield 1.15 gram. (96%). $^1$H NMR(DMSO—$d_6$): δ 3.5 (br m, PEG), 7.49 (d, aromatic), 7.95 (d, aromatic), 8.60 (t, PEG—N$\underline{H}$CO—).

Example 4
Preparation of mPEG—NTH—COO-Drug

Example 5
Synthesis of mPEG Phenyl ether-p-mexiletine Carbamate

MPEG phenyl ether-p-succinimidyl carbonate (300 mg, 5000 Dalton), and mexiletine hydrochloride (16 mg), TEA (20 μl) were dissolved in 8 ml of anhydrous methylene chloride. The solution was stirred overnight. The solvent was condensed on a rotary evaporator and 100 ml of isopropyl alcohol was added to the residual syrup. The resulting precipitate was collected by filtration, washed with 20 ml of ether, and dried in vacuo. $^1$H NMR(DMSO—$d_6$):

20 mg of the above drug was azeotropically dried in pyridine and methoxy-PEG isocyanate (177 mg, 5000 Dalton) was then added. The solution was stirred at room temperature overnight and the solvent was removed under reduced pressure to yield a residual syrup. To this was added 100 ml of ether and the resulting precipitate was collected by filtration and dried in vacuo. PEG conjugation was demonstrated to be 60% by $^1$H NMR and GPC.

δ3..5 (br m, PEG) 2.23 (s, CH3—), 6..9 (M, aromatic H), 1.23 (d,—CH2—CH(CH3)—). Conjugation was shown to be greater than 90% by GPC.

Example 6
Modification of Lysozyme with the PEG Derivatives in Examples 1–3

5–25 mg of each of the PEG derivatives prepared in Examples 1–3 was mixed with 1 ml of lysozyme solution at pH 7 (5 mg/ml in 0.1 M phosphate buffer). The solution was gently shaken for 5 hours at room temperature, and then stored at +4° C. for future analysis. PEGylation was monitored by capillary electrophoresis.

Example 7
Monitoring Hydrolysis of the PEG Conjugate of Lysozyme by Capillary Electrophoresis.

Figure 1:
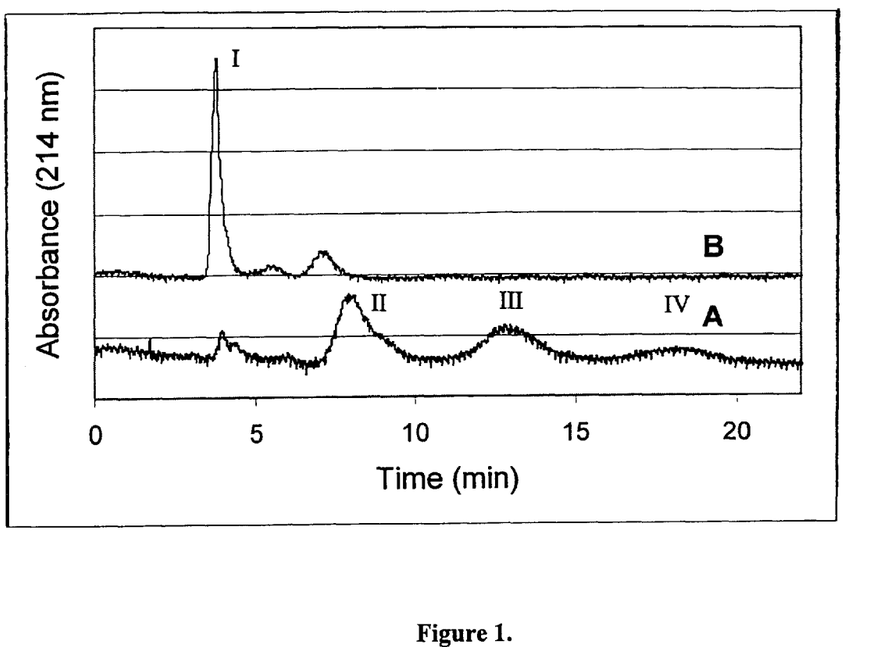
FIG. 1 is a CE graph showing the hydrolysis of mPEG-lysozyme conjugate prepared with N-mPEG benzamide-m-succimidyl carbonate. At time zero, a small amount of free lysozyme was mixed with mono, di, and tri PEGylated lysozyme (Curve A). After hydrolysis for 10 days at pH 7 and 37° C., more than 85% of free lysozyme was released (Curve B). Peaks I, II, III, and IV represent free lysozyme, mono-PEGylated lysozyme, di-PEGylated lysozyme and tri-PEGylated lysozyme, respectively.

The conjugates prepared as described above were placed at 37° C. and at room temperature and hydrolysis was monitored by capillary electrophoresis (CE). The CE graphs are shown in FIG. 1.

CE conditions: A solution of 25 mM phosphate buffer, containing 0.1 mg/ml PEO 600K, pH 2.7 was flushed through the capillary for approximately 15–20 min. A voltage of 15 kV was applied until a smooth baseline was obtained. The 25 mM phosphate buffer solution was again flushed through for approximately 5 min and the capillary was then ready for sample injection. The sample, which was adjusted to pH 2 by a phosphate buffer (0.1 M, pH 2), was injected hydrostatically for about 10 sec at a height of approximately 6 inches. A voltage of 15 kV was applied throughout the run with a current between 24 and 30 $\mu$A. The protein and PEG-protein conjugate were detected by a UV monitor at 214 nm. The CE instrument consists of a high-voltage power supply (Spellman CZE1000R), a fused silica capillary (75 $\mu$m i.d., 360 $\mu$m o.d., Polymicro Technologies, Phoenix, Ariz.) and a linear 200 UV/VIS monitor supplied with a deuterium lamp and a capillary flow cell. The total length of the capillary was 64.5 cm, with a 1 cm optical window at 40 cm from the anode. UV data was retrieved and stored using LabVIEW version 4.0.1 software (National Instruments).

Example 8
Analysis of Hydrolysis Product by MALDI-TOF

The hydrolysis product from each conjugate was examined by MALDI-TOF to determine if there was any dimerization caused by reactions between hydrolysis intermediates. Free lysozyme was used as control. No dimerization was observed.

Experiment 9
Bioactivity Measurement of Reversible Lysozyme Conjugate

Bioactivity of free lysozyme, PEG conjugates of lysozyme and lysozyme recovered from hydrolysis of the conjugates were measured by an assay from the standard protocol of Sigma for hen's egg white (HEW) lysozyme EC.3.2.1.17. A solution containing the unmodified or PEG-modified lysozyme was diluted to 5.5 $\mu$g/ml in a 66 mM sdium phosphate buffer (pH 6.24). A suspension of 1.5 mg Micrococcus lysodeikticus in 10 ml of 66 mM phosphate buffer (pH 6.24) was allowed to equilibrate at room temperature until the absorbance at 450 nm was constant. Then 0.1 ml of a lysozyme solution was placed in a 1 cm light path quatz cuvette containing 2.5 ml of the substrate suspension. The decrease in the absorbance at 450 nm was recorded and the activity was determined from the maximum linear rate. Eighty-two percent of lysozyme bioactivity was recovered from the m-PEG-lysozyme conjugate, while the mPEG lysozyme had undetectable bioactivity prior to hydrolysis.

Example 10
Preparation of Hydrogels From Di-functional PEG 3400 benzamide-m-succimidyl Carbonate In a test tube, 55 mg of di-functional PEG 3400 benzamide-m-succimidyl carbonate was dissolved in 0.36 ml of cold de-ionized water (4° C.). Then 0.36 ml of 8-arm-PEG amine 10,000 (Shearwater Polymers, Inc, Ala., USA) solution (110 mg/ml, in pH 7 phosphate buffer) was added. After rapid mixing, the solution was allowed to stand at room temperature. A clear gel formed in a few minutes.

Example 11
Degradation of the Hydrogels Prepared from Di-functional PEG benzamide-m-succimidyl Carbonate An approximately 0.2 cm$^3$ piece of gel prepared from Example 8 was put into about 1 ml of PBS buffer, while the other was put into the same amount of human serum. Both samples were incubated at 37° C. Gel degradation was monitored visually to evaluate the degradation life times. The gel was observed to degrade to yield a clear solution in approximately 4 hours.

Although the foregoing invention has been described in some detail by way of illustration and example for purposes of clarity of understanding, it will be obvious that certain changes and modifications may be practiced within the scope of the appended claims.

That which is claimed is:

1. A hydrolytically degradable hydrogel comprising a backbone bonded to a crosslinking agent through a hydrolyzable carbamate linkage, wherein said backbone comprises at least two amino groups, and wherein said crosslinking agent is selected from the group consisting of:

and wherein

POLY is a water soluble, non-peptidic polymer;

L and L' are hydrolytically stable linkages;

Ar and Ar' are aromatic groups;

Z is a central branched core moiety;

n is from 2 to about 100; and

X and X' are activating groups capable of reacting with said amino groups to form said hydrolyzable carbamate linkages.

2. The hydrogel of claim 1, wherein said POLY is a poly(ethylene glycol) having a molecular weight of at least 20,000.

3. The hydrogel of claim 1, wherein L and L' are selected from the group consisting of ethers, amines, imides, esters, amides, carbamides, imines and thioesters.

4. The hydrogel of claim 1, wherein L and L' are —O— or —HNCO—.

5. The hydrogel of claim 1, wherein Ar and Ar' are selected from the group consisting of phenyl, substituted phenyl, biphenyl, substituted biphenyl, polycyclic aryls, substituted polycyclic aryls, heterocyclic aryls, and substituted heterocyclic aryls.

6. The hydrogel of claim 1, wherein X and X' are selected from the group consisting of halogen, N-succinimidyloxy, 1-benzotriazolyloxy, 1-imidazolyloxy, and p-nitrophenyloxy.

7. The hydrogel of claim 1, wherein said backbone is selected from the group consisting of proteins, glycoproteins, phosphorylated proteins, acylated proteins, peptides, aminocarbohydrates, glycosaminoglycans, aminolipids, poly(vinylamine), polylysine, poly(ethylene glycol) amines, and pharmaceutical agents having at least two amino groups.

8. The hydrogel of claim 1, wherein Z is selected from the group consisting of lysine, glycerol, pentaerythritol, and sorbitol and their oligomers.

9. A delivery system for delivering a biologically active agent comprising the biologically active agent carried within a hydrolytically degradable hydrogel, wherein said hydrogel comprises a backbone bonded to a crosslinking agent through a hydrolyzable carbamate linkage, said backbone having at least two amino groups, said crosslinking agent being selected from the group consisting of:

and wherein

POLY is a water soluble, non-peptidic polymer;

L arid L' are hydrolytically stable linkages;

Ar and Ar' are aromatic groups;

Z is a central branched, core moiety;

n is from 2 to about 100; and

X and X' are activating groups capable of reacting with said amino groups to form said hydrolyzable carbamate linkages.

10. The delivery system of claim 9, wherein said POLY is a poly(ethylene glycol).

11. The delivery system of claim 9, wherein L and L' are —O— or —HNCO—.

12. The delivery system of claim 9, wherein Ar and Ar' are selected from the group consisting of phenyl, substituted phenyl, biphenyl, substituted biphenyl, polycyclic aryls, substituted polycyclic aryls, heterocyclic aryls, and substituted heterocyclic aryls.

13. The delivery system of claim 9, wherein X and X' are N-succinimidyloxy.

14. The delivery system of claim 9, wherein said backbone is selected from the group consisting of proteins, glycoproteins, phosphorylated proteins, acylated proteins, peptides, aminocarbohydrates, glycosaminoglycans, aminolipids, poly(vinylamine), polylysine, poly(ethylene glycol) amines, and pharmaceutical agents having at least two amino groups.

15. The delivery system of claim 9, wherein Z is selected from the group consisting of lysine, glycerol, pentaerythritol, and sorbitol and their oligomers.

16. The delivery system of claim 9, wherein said biologically active agent is covalently linked to the hydrogel.

17. The hydrogel of claim 1, wherein POLY is a poly(ethylene glycol) having a molecular weight of about 200 to about 100,000 Da.

18. The hydrogel of claim 1, wherein POLY is selected from the group consisting of poly(alkylene oxides), copolymers of ethylene glycol and propylene glycol, poly(oxyethylated polyols), poly(vinyl alcohol), carbohydrate-based polymers, and random or block copolymers and terpolymers based on monomers of these polymers.

19. The hydrogel of claim 1, wherein POLY is selected from the group consisting of poly(ethylene glycol), polypropylene glycol, copolymers of ethylene glycol and propylene glycol, poly(oxyethylated glycerol), poly(oxyethylated sorbitol), poly(oxyethylated glucose), poly(vinyl alcohol), dextran, poly(oxazoline), poly(acryloylmorpholine), and poly(vinylpyrrolidone).

20. The hydrogel of claim 1, wherein POLY is selected from the group consisting of linear, branched, forked, and degradable poly(ethylene glycol).

21. The hydrogel of claim 1, wherein Ar and Ar' are each ortho-, meta- or para-substituted phenylene.

22. The hydrogel of claim 1, wherein both L and L' are selected from the group consisting of —O—, —NR— where R is H, $C_{1-6}$ alkyl or $C_{1-6}$ substituted alkyl, —$CO_2$—, —$O_2C$—, —$O_2CO$—, —CONH—, —NHCO—, —S—, —SO—, and —$SO_2$—.

23. The hydrogel of claim 1, wherein the backbone is a macromolecule.

24. The hydrogel of claim 1, wherein the backbone is selected from the group consisting of fibrin, fibrinogen, thrombin, albumin, globulin, collagen, fibronectin, and chitosan.

25. The hydrogel of claim 1, wherein the backbone is a microorganism.

26. The hydrogel of claim 1, wherein Z is a polyol.

27. The hydrogel of claim 1, wherein the crosslinking agent has the formula:

wherein PEG is poly(ethylene glycol).

28. The delivery system of claim 9, wherein POLY is a poly(ethylene glycol) having a molecular weight of about 200 to about 100,000 Da.

29. The delivery system of claim 9, wherein POLY is selected from the group consisting of poly(alkylene oxides), copolymers of ethylene glycol and propylene glycol, poly(oxyethylated polyols), poly(vinyl alcohol), carbohydrate-based polymers, and random or block copolymers and terpolymers based on monomers of these polymers.

30. The delivery system of claim 9, wherein POLY is selected from the group consisting of poly(ethylene glycol), polypropylene glycol, copolymers of ethylene glycol and propylene glycol, poly(oxyethylated glycerol), poly(oxyethylated sorbitol), poly(oxyethylated glucose), poly(vinyl alcohol), dextran, poly(oxazoline), poly(acryloylmorpholine), and poly(vinylpyrrolidone).

31. The delivery system of claim 9, wherein POLY is selected from the group consisting of linear, branched, forked, and degradable poly(ethylene glycol).

32. The delivery system of claim 9, wherein Ar and Ar' are each ortho-, meta- or para-substituted phenylene.

33. The delivery system of claim 9, wherein both L and L' are selected from the group consisting of —O—, —NR— where R is H, $C_{1-6}$ alkyl or $C_{1-6}$ substituted alkyl, —$CO_2$—, —$O_2C$—, —$O_2CO$—, —CONH—, —NHCO—, —S—,—SO—, and —$SO_2$—.

34. The delivery system of claim 9, wherein the backbone is a macromolecule.

35. The delivery system of claim 9, wherein the backbone is selected from the group consisting of fibrin, fibrinogen, thrombin, albumin, globulin, collagen, fibronectin, and chitosan.

36. The delivery system of claim 9, wherein the backbone is a microorganism.

37. The delivery system of claim 9, wherein Z is a polyol.

38. The delivery system of claim 9, wherein the biological active agent is selected from the group consisting of enzymes, proteins, peptides, aminolipids, polysaccharides having an amino group, and amino-oligonucleotides.

* * * * *

UNITED STATES PATENT AND TRADEMARK OFFICE
CERTIFICATE OF CORRECTION

PATENT NO.    : 6,541,015 B2
DATED         : April 1, 2003
INVENTOR(S)   : Bentley et al.

It is certified that error appears in the above-identified patent and that said Letters Patent is hereby corrected as shown below:

Column 15,
First line after "Example 4", "NTH" should read -- NH --.

Column 19,
Line 26, after "branched" cancel the comma ",".

Column 20,
Line 24, in the formula, "POLY" should read -- PEG --.
Line 62, "biological" should read -- biologically --.

Signed and Sealed this

Twenty-sixth Day of August, 2003

JAMES E. ROGAN
*Director of the United States Patent and Trademark Office*